United States Patent [19]

Chang et al.

[11] Patent Number: 5,084,350

[45] Date of Patent: Jan. 28, 1992

[54] METHOD FOR ENCAPSULATING BIOLOGICALLY ACTIVE MATERIAL INCLUDING CELLS

[75] Inventors: Thomas M. S. Chang, St-Lambert; Harry Wong, Winnipeg, both of Canada

[73] Assignee: The Royal Institution for the Advance of Learning (McGill University), Quebec, Canada

[21] Appl. No.: 480,901

[22] Filed: Feb. 16, 1990

[51] Int. Cl.⁵ .................... C12N 11/04; C12N 11/10; B01J 13/14; B01J 13/02

[52] U.S. Cl. ................................. 428/402.2; 264/4.1; 264/4.32; 264/4.33; 435/178; 435/182; 435/240.22

[58] Field of Search ....................... 264/4.32, 4.33, 4.6; 427/213.31, 213.32, 213.35; 428/402.2; 435/178, 182, 240.22

[56] References Cited

U.S. PATENT DOCUMENTS

| | | | |
|---|---|---|---|
| 4,352,883 | 10/1982 | Lim | 435/182 X |
| 4,663,286 | 5/1987 | Tsang et al. | 435/178 |
| 4,744,933 | 5/1988 | Rha et al. | 264/4.3 |
| 4,789,516 | 5/1988 | Lim | 264/4.32 |
| 4,833,081 | 5/1989 | Walker | 435/182 |
| 4,923,645 | 5/1990 | Tsang et al. | 264/4.3 |
| 4,927,761 | 5/1990 | Reading et al. | 435/178 |
| 4,942,129 | 7/1990 | Goosen et al. | 435/182 |
| 4,956,128 | 9/1990 | Hommel et al. | 435/178 X |

OTHER PUBLICATIONS

Chang, T. M. S., *Science*, 1964, 146:524–525.
Chang, T. M. S., "Semipermeable Aqueous Microcapsules," 1965, Ph.D. Thesis, McGill University.
Chang, T. M. S. et al., *Can J. Physiol. Pharmacol.*, 1966, 44:115–28.
Chang, T. M. S., *Artifical Cells*, 1972, Springfield, IL., U.S.A., Charles C. Thomas Publishers.
Sun A. M. et al., *Appl. Biochem. Biotechnol.*, 1984, 10:87–99.
Wong, H. and Chang, T. M. S., *Biomat, Art Cells Art. Org.*, 1988, 16:731–39.
Seglen P. O., *Methods, Cell Biol.*, 1976, 13:29–83.
Smedsrod S. et al., *J. Leuk. Biol.*, 1985, 38:213–30.

*Primary Examiner*—Richard D. Lovering
*Assistant Examiner*—John M. Covert
*Attorney, Agent, or Firm*—Nixon & Vanderhye

[57] ABSTRACT

Method for encapsulating biologically active material within a semipermeable capsule wherein gelled beads are obtained by suspending the material in a solution of a water-soluble substance which can be reversibly gelled, forming the solution into droplets and gelling the droplets to produce discrete shaped-retaining temporary gelled beads. The improvement comprises the subsequent steps of (a) suspending the gelled beads in a solution of a water-soluble substance which can be reversibly gelled (b) forming droplets from the suspension of (a), thereby obtaining droplets which contain one or more gelled beads of step (a); (c) gelling the droplets of step (b) to produce discrete shaped-retaining temporary gelled beads which contain the gelled beads of step (a); (d) forming semi-permeable membranes on each of the gelled beads of step (c), thereby preventing the incorporation of any biologically active material of step (a) into the membranes and (e) reliquifying the gel within the membranes, thereby dispersing the content of the gelled beads of step (a) within the capsule.

16 Claims, 2 Drawing Sheets

STANDARD METHOD

NOVEL METHOD

METHOD FOR ENCAPSULATING BIOLOGICALLY ACTIVE MATERIAL INCLUDING CELLS

BACKGROUND OF THE INVENTION

With the first development of artificial cells (Chang, T.M. S., *Science*, 1964, 146:524–525), the microencapsulation of biological materials has become an area of study for industrial processes and biomedical research. In 1965, T. M. S. Chang devised the first method for cell encapsulation (Chang, T. M. S., "semipermeable aqueous microcapsules," 1965, Ph.D. Thesis, McGill University; Chang, T. M. S. et al., *Can J. Physiol. Pharmacol.*, 1966, 44:115-28) and proposed the encapsulation of endocrine cells such as pancreatic or hepatic cells for treating pancreatic and liver disorders (Chang, T. M. S., *Artifical Cells*, 1972, Springfield, Ill., U.S.A., Charles C. Thomas Publishers). A. M. Sun et al. later demonstrated that intra-peritoneally implanted polylysine-alginate microcapsules containing pancreatic islet cells can temporarily maintain normal blood glucose levels in diabetic rats (Sun A. M. et al., *Appl. Biochem. Biotechnol.*, 1984, 10:87-99). When these encapsulated islets were implanted into different animal species such as mice, there was severe aggregation and clumping of the microcapsules. This caused these islets to stop functioning.

For our transplantation studies, we encapsulated rat hepatocytes within the same alginate-polylysine microcapsules used by Sun, A. M. et al. After implantation in mice, we saw severe aggregation of the microcapsules. As determined by trypan blue stain exclusion, cell viability was only noted in the non-aggregated and free floating microcapsules (Wong, H. and Chang, T. M. S., *Biomat Art Cells Art. Org.*, 1988, 16:731-39).

Our studies also showed cells embedding within the microcapsule membrane matrix and protruding from the surface of the microcapsule membrane. These resulted into two major problems. First, the protruding cells can break away and leave holes in the microcapsule membrane. This lets some encapsulated contents to escape out of the microcapsule. Secondly, the protruding cells that remained embedded in the membrane do not get entirely covered by the microcapsule membrane. Thus, these cells are exposed to the outsides of the microcapsule. In addition, poly-l-lysine is biologically reactive. In normal situation, it is covered by a layer of alginate and rendered unobtrusive. Therefore, around the holes and around the cells protruding from the membrane, some of the reactive poly-l-lysine becomes uncovered. The combined effects of these three problems therefore leads to a cascade of immunological events and bioincompatibility which result in host rejection and premature microcapsule aggregation. Therefore, the method of cell encapsulation using the standard polylysine-alginate procedure is not suitable for use in transplantation.

Further 'in vivo' studies showed that most of the standard microcapsules containing rat hepatocytes aggregate into clumps when implanted intra-peritoneally into mice. Thus, progressively with time, a fewer number of free unaggregated microcapsules were recovered by periotoneal lavage. In contrast, in mice implanted with blank alginate-polylysine microcapsules containing no cells, there was observed little to no aggregation of the blank microcapsules. There was a greater degree of incompatibility among the hepatocyte containing microcapsules. In hepatocyte loaded microcapsules, we observed cells entrapped in the membrane matrix, and cells protruding from the membrane surface. This exposes the cells to immunological rejection and also exposing some polylysine with resulting bioincompatibility. The result is the aggregation and rejection of the microcapsules. Therefore, cells microencapsulated by the standard polylysine-alginate method cannot function after implantation.

The Japanese Patent Application S.N. 58/189,031, published on Nov. 4, 1983, discloses a method to obtain double microcapsules, which a very similar method was already published by T. M. S. Chang (Chang, T. M. S., 1965, Ph.D. Thesis, 'ibid'; Chang, T. M. S. et al., *Can J. Physiol. Pharmacol.*, 1966, 'ibid'; Chang, T. M. S., *Artifical Cells*, 1972, 'ibid').

There is disclosed large microcapsules each containing a number of smaller microcapsules. The smaller microcapsules remain as permanent microcapsules made of permanent outer polymer membranes.

The resulting large microcapsules, although devoided of any encapsulated material embedded within their membrane, have the following three barriers to permeability for the diffusion of substances into and out of the smaller microcapsules:

1) the membrane of the larger microcapsule;
2) the membrane of the smaller microcapsules located within the large one; and
3) the space between the membrane of the larger microcapsule and the membrane of the smaller microcapsules.

In microcapsulation of cells, these permeability barriers will adversely affect the following:

1) the exchange of the nutrients required for the growth of the encapsulated cells;
2) the removal of the waste products of the encapsulated cells;
3) the response of the encapsulated cells will be delayed. For example, the response of encapsulated islets of Langerhams in secreting insulin, according to the change in blood glucose concentration, will be delayed and out of sequence; and
4) the low permeability which causes other problems.

Multiple coating and multiple membrane layers around each microcapsule can also prevent cells from embedding in the outer membrane. However, these multiple membranes layer would have problems similar to the double microcapsules. Each layer contributing to the increase in barrier to permeability. The more there is membrane layers, the less permeability is observed.

It would be highly desirable if there could be provided a novel method of microencapsulation of biological materials which would overcome all the problems of the standard methods.

That is, if there could be provided a microcapsule where no cells or biological materials is seen protruding nor entrapped within the capsule membrane matrix and where its permeability is not hampered.

Also, it would also be highly desirable to have a microcapsule which does not tend to aggregate after its implantation.

SUMMARY OF THE INVENTION

Surprisingly and in accordance with the present invention, there is provided a method to produce a microcapsule which is devoided of any cells or biologically active material embedded within or protruding from its membrane matrix. The microstructure obtained in accordance with the present invention does not have an hampered permeability for the diffusion of nutrients or metabolites of the encapsulated cells or biologically active material.

There is provided in a method for encapsulating biologically active material within a semipermeable capsule wherein small gelled beads are obtained by suspending said material in a solution of a water-soluble substance which can be reversibly gelled, forming said solution into small droplets, and gelling said droplets to produce discrete shape-retaining temporary small gelled beads; the improvement comprising the subsequent steps of:

a) suspending said small gelled beads in a solution of a water-soluble substance which can be reversibly gelled;

b) forming large droplets from the suspension of step a), thereby obtaining large droplets which contain one or more small gelled beads;

c) gelling said large droplets to produce discrete shape-retaining temporary large gelled beads which contain said small gelled beads;

d) forming semi-permeable membranes on each large gelled beads of c), thereby preventing the incorporation of any biologically active material of the smaller gelled beads into said membranes; and e) reliquifying the gel within said membranes, thereby dipersing the content of said smaller gelled beads within said capsule.

Also, there is provided a semipermeable capsule obtained according to the method of the present invention characterized in that its membrane is devoided of any encapsulated material embedded or protruding therein. A very high concentration of cells or material can be encapsulated without the encapsulated material embedded or protruding therein.

Finally, there is provided an artificial organ suitable for implantation in a mammalian host which comprises at least one capsule obtained according to the method of the present invention and containing one or more viable, healthy physiologically active living tissue cells or other biologically active material, said capsule being impermeable to said host immune system proteins or immune system cells but permeable to tissue nutrients and to metabolites or secretion produced by said encapsulated tissue or biologically active material, thereby said artificial organ being devoided of aggregation of capsules and of immunological reactions of said host.

Although the present invention has been described in the foregoing description by way of preferred embodiments thereof, it should be pointed out that it can be modified at will, within the nature of the present invention.

IN THE DRAWINGS

DETAILED DESCRIPTION OF THE INVENTION

The method of encapsulating biologically active material of the present invention overcomes all the previous problems of implantation and permeability by providing a microcapsule devoided of any material embedded or protruding from its membrane matrix.

The membrane defects associated with the standard method of microencapsulation are eliminated by the novel method of the present invention. With this method, high cell densities in the capsule can be acquired. Here, the encapsulated material is entrapped within a matrix that does not become part of the capsule membrane. This was achieved by entrapping the smaller microbeads containing the cells within a larger capsule. Upon the formation of the capsule, the matrix of the microbeads are then solubilized, thus releasing the contents of the microbead to float freely within the interior of the capsule. As seen in FIGS. 1B and 2B all the entrapped cells are within the capsule and no protruding cells are observed, unlike for the standard method of encapsulation.

Figure 1A:
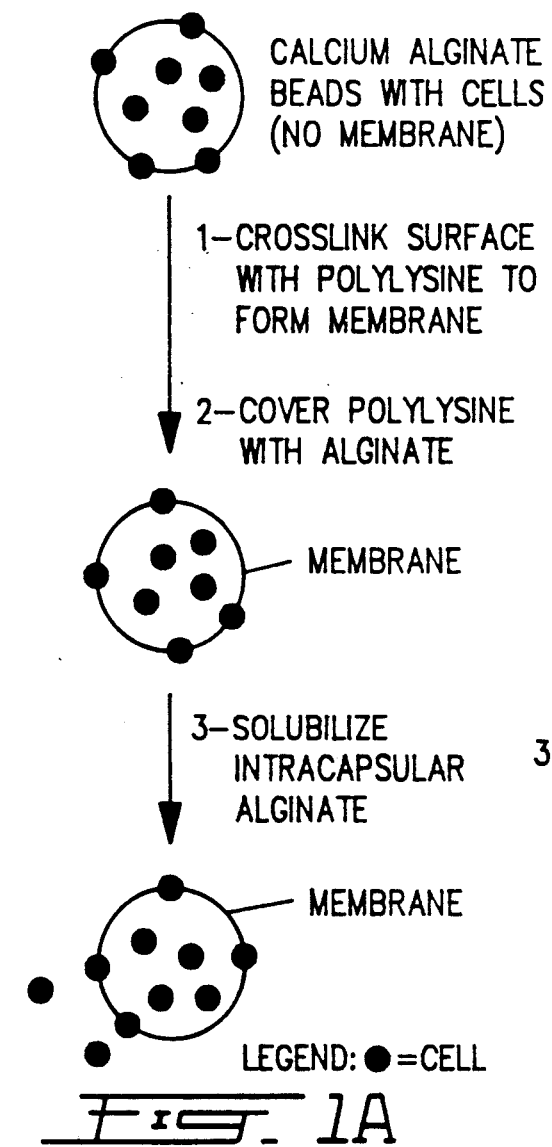
FIGS. 1A and 1B shows a comparison between the standard method of encapsulation (1A) and the method of encapsulation in accordance with the present invention (1B)
Figure 1B:
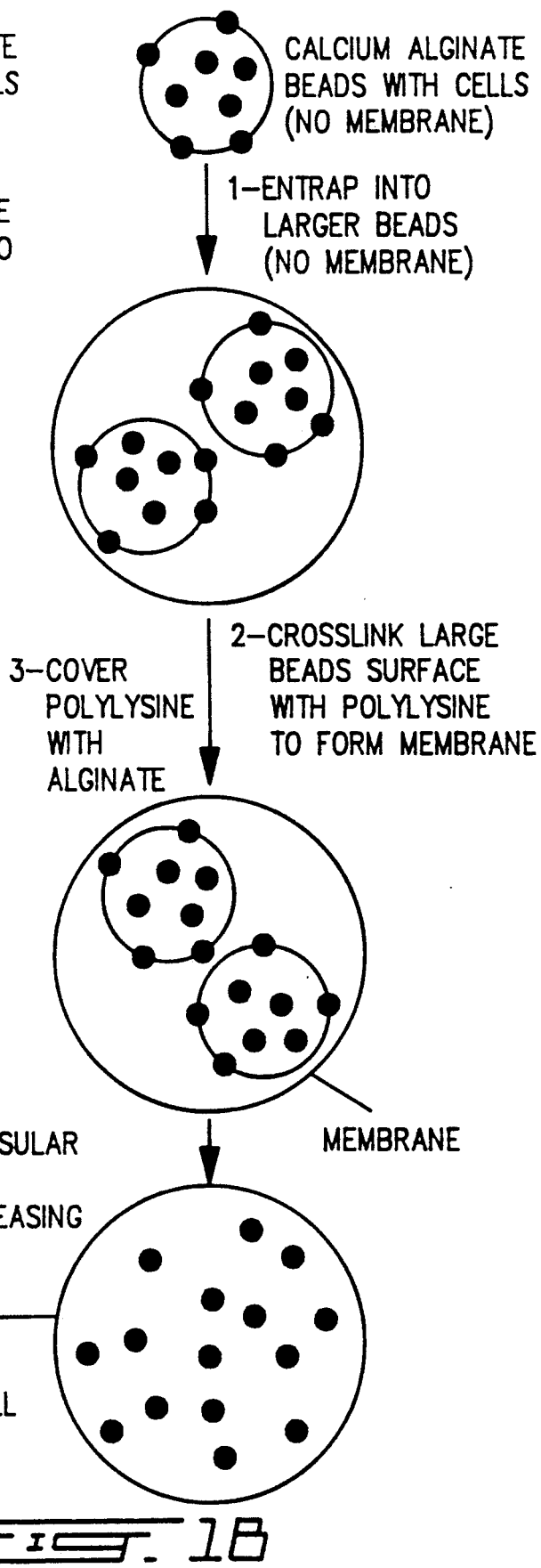
Figure 2A:
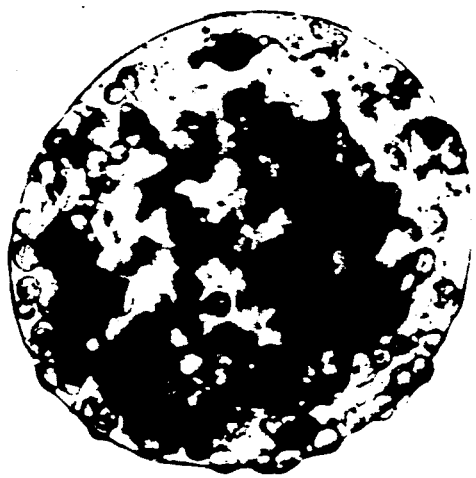
FIGS. 2A and 2B shows light microscope pictures of a microcapsule prepared by the standard alginate-polylysine-alginate method (2B) v. microcapsules prepared by the novel method (2B).
Figure 2B:

As illustrated in FIGS. 1A and 2A using the standard process of microencapsulation, cells are embedded within the membrane matrix or protrude from the membrane surface. When the intracapsular calcium alginate is solubilized, some of the cells which protrude from the membrane surface are seen to escape into the suspending fluid. When these microcapsules are implanted intra-peritoneally into animals, severe aggregation occurs.

The biologically active material to be encapsulated including tissues, organelles or cells, is prepared in accordance with well-known prior art techniques in finely divided form and suspended in aqueous medium suitable for maintenance and for supporting the ongoing metabolic processes of the particular tissue involved. Media suitable for this purpose are commercially available. The dimension of the material to be encapsulated can vary widely between 2,000 daltons and 2 mm in diameter.

As biologically active material which can be encapsulated in accordance with the present invention, there may be mentioned the following: viable cells such as liver cells including hepatocytes and Kupffer cells; endocrine cells including thyroid cells and pancreatic cells including islet cells; platelets; thyroid tissue cells; erythrocytes; leucocytes and other cells; viable tissues such as endocrine tissues including pancreatic tissues and thyroid tissues; other viable tissues including liver tissues; proteins including enzymes; albumin; immunoproteins; antibodies; antigens; hormones; peptides; drugs; organelles and microorganisms.

The material used to form the temporary capsules may be selected from any non-toxic, water-soluble material which, by a change in the surrounding temperature, pH, or ionic environment, or concentration, can be converted to a shape retaining mass. Preferably, the material also contains plural, easily ionized groups, such as carboxyl or amino groups, which can react by salt formation with polymers containing plural groups which ionize to form species of opposite charge. As will be explained below, this type of material enables the deposition of a permanent membrane of a selected porosity and of a selected 'in vivo'.

The presently preferred materials for forming the temporary capsule are water-soluble, natural or synthetic polysaccharide gums. Many such materials are commercially available. They are typically extracted from vegetable matter and are often used as additives to various foods. Sodium alginate is the presently preferred water-soluble gum. Other usable gums include guar gum, gum arabic, carrageenan, pectin, gelatin, iragacanth gum, xanthan gum, or their acidic fractions.

These materials comprise glycoside-linked saccharide chains. Many contain free acid groups, which are often present in the alkali metal ion form, e.g. sodium form. If a multivalent ion such as calcium or strontium is exchanged for the alkali metal ion, the liquid, water-soluble polysaccharide molecules are "crosslinked" to form a water insoluble, shape-retaining gel which can be resolubilized on removal of the ions by ion exchange or via a sequestering agent. While essentially any multivalent ion which can form a salt is operable, it is preferred that physiologically compatible ions, e.g. calcium, be employed. This tends to preserve the tissue in the living stage. Other multivalent cations can be used for less fragile material.

Other gums can be switched between the water soluble and gelled, water insoluble state simply by changing the pH of the medium in which they are dissolved.

A typical tissue-tissue medium-gum solution composition comprises equal volumes of tissue in its medium and a one to two percent solution of gum in physiological saline. When employing sodium alginate, a 1.0 to 1.5 percent solution has been used with success.

When encapsulating materials which can resist changes in temperature, gelatin or agar may be used to form the temporary capsules. These can be gelled by injection into a low temperature environment. Other water soluble substances such as hydroryethyl methacrylaic may also be used.

In the next step of the encapsulating process, the gum solution containing the tissue is formed into droplets of a desired size. Thereafter, the droplets are immediately gelled to form shape-retaining spherical or spheroidal masses.

Broadly, the small gelled beads may vary in diameter between $1\mu$ and 1 mm.

In accordance with the present invention, the shape-retaining temporary small gelled beads are further encapsulated to obtain large droplets which contain one or more small gelled beads. The large droplets are then gelled.

Broadly, the large gelled beads may vary in diameter between $2\mu$ and 10 mm. Appreciating that depending on the diameter of the small gelled beads, the diameter of the large gelled beads could be smaller than 1 mm.

The preferred diameter of small and large gelled beads depend on its intended usage. When cells are encapsulated, the preferred diameter of small gelled beads is about 0.5 mm and that of large gelled beads is about 1 mm. When enzymes or proteins are encapsulated, the preferred diameter of small gelled beads is about $50\mu$ and that of large gelled beads is about $100\mu$.

In the next step of the process, a semipermeable membrane is formed about the surface of the temporary large gelled beads. There are a variety of methods available for effecting this step, some of which are known in the art. For example, interfacial polymerization techniques can be used. In interfacial polymerization, a pair of at least difunctional reactive monomers or a monomer and a relatively low molecular weight polymer, one of which is soluble in polar solvent such as water and the other of which is soluble in hydrophobic solvents such as hexane, are caused to react at the interface of an emulsion of the water-in-oil type.

Other techniques to formed the membrane on the surface of the temporary gelled beads include interfacial coacervation, cross-linked proteins and those formed from hydrogel.

The preferred method of forming the semipermeable membrane is to permanently crosslink the surface layers of the large droplets by subjecting them to an aqueous solution of a polymer containing groups reactive with functional groups in the gel molecules. Certain long quaternary ammonium salts or polymer containing quaternary ammonium groups may be used for this purpose in some circumstances. When acidic gums are used, polymer containing acid reactive groups such as polyethylenimine, polylysine, polyornithine and polyarginine. In this situation, the polysaccharides are crosslinked by interaction between the carboxyl groups and the amine groups. Advantageously, permeability can be controlled by selecting the molecular weight of the crosslinking polymer used. For example, a solution of polymer having a low molecular weight, in a given time period, will penetrate further into the temporary gelled bead, then will a high molecular weight polymer.

The degree of penetration of the crosslinker has been correlated with the resulting permeability. In general, the higher the molecular weight of the polymer and the less penetration of the temporary gelled beads will cause membranes with larger pore size. Broadly, polymers within the molecular range of 3,000 to 100,000 daltons or greater may be used depending on the duration of the reaction, the concentration of the polymer solution and the degree of permeability desired. One successful set of reaction conditions using polylysine of average molecular weight of about 35,000 daltons, involved a reaction for two minutes, with stirring of a physiological saline solution containing 0.0167% polylysine. Those skilled in the art can easily determine the optimal reaction conditions suitable for controlling permeability in a given system.

Polymers vary with respect to the rate at which they can be dispersed 'in vivo': some are digested without any difficulty, others are slowly degraded, and others remain indefinitely.

The microcapsules produced in accordance with the present invention have a selected 'in vivo' lifespan, ranging generally between a few hours or days to substantial permanence. Again, those skilled in the art will be able to produce microcapsules of a selected 'in vivo' lifespan empirically without the exercise of invention in view of this disclosure.

The last step of the method of the present invention consists in reliquifying the gel inside the membrane to its water soluble form. This may be done by reestablishing the conditions under which the gum is a liquid, either by changing the pH of the medium or removing the calcium or other multifunctional cations used. In the gels which are insoluble in the presence of multivalent cations, the medium in the capsule can be resolubilized simply by immersing the capsules in phosphate buffered saline which contains alkali metal ions and hydrogen ions. When monovalent ions exchange with the calcium or other multifunctional ions are found within the gums, the capsules are immersed in the solution with stirring. Other salts, such as sodium citrate, EDTA (ethylenediaminetetraacidic acid) may be used for the same purpose.

Broadly, the microcapsules obtained in accordance with the method of the present invention and containing for example a tissue can be injected into an appropriate site within a host, for the purpose of providing the host body, at least temporarily, with the tissue's specialized physiological function. Such a use of the microcapsule can be referred to an artificial organ. The artificial organ has the advantages of obviating the need for surgical implantation (although microcapsules may be implantated surgically if desired) and successfully dealing with the problems of immune rejection and natural physical isolation.

The present invention will be more readily understood by referring to the following examples which are given to illustrate the invention rather than to limit its scope.

EXAMPLE I

Materials

Low viscosity sodium alginate (Keltone LV®), M.Wt. range from 12,000 to 80,000, was obtained from Kelco, Division of Merck & Co. (Clark, N.J.). The reagents poly-l-lysine (HBr), M.Wt. (vis.) range from 15,000 to 30,000; type IV collagenase; type I-S trypsin inhibitor, and D-fructose were purchased from Sigma Chemical Co. (St. Louis, Mo.). Percoll® (1.129 g/ml) was purchased from Pharmacia P-L Biochemicals (Montreal, Qc.). Analytical grade reagents such as sodium chloride, sodium hydroxide, calcium chloride di-hydrate, and tri-sodium citrate were obtained from various commercial sources. All solutions were prepared with non-pyrogenic and sterile water or saline (0.9% sodium chloride) respectively purchased from Baxter Corp. (Toronto, Ont.), or Travenol Canada Inc. (Mississauga, Ont.); and buffered with HEPES (4-(2-hydroxyethyl)-1-piperazine ethane sulphonic acid) buffer (Boehringer Mannheim, Montreal, Qc.). William's E medium (Gibco; Burlington, Ont.) was used for hepatocyte isolation. It was supplemented with streptomycin and penicillin (Gibco Laboratories; Burlington, Ont.).

Two different droplet generators were implemented for the encapsulation of cells within macrocapsules. The first droplet generator, which was used for making the microbeads, consisted of 2 co-axially arranged jets. The diameter of the central sample jet was equivalent to a 26 G stainless steel needle purchased from Perfektum (Popper & Sons, Inc., New Hyde Park, N.Y.). Sterile air was passed through a surrounding jet that was 16 G in diameter. To prevent extruding sample from occluding the outlet of the surrounding air jet, the tip of the sample jet was constructed such that the tip of the sample jet projected 0.5 mm beyond the end of the air jet.

Although larger and modified, the second droplet generator was constructed similarly to the first droplet generator described above. The second droplet generator had a 13G sample jet, a 8G surrounding air jet; and the ends of the jets were cut flush to each other. A 1.7×1.1 mm PTFE capillary tube (Pharmacia P-L Biochemicals; Montreal, Qc.) was inserted into the sample jet until it protruded approximately 15 mm from the outlet of the sample jet. The end of the capillary tubing was sufficiently tapered to facilitate shearing by the flow of passing air from the air jet. The capillary tubing was approximately 3.2 m in length, and had the capacity to be filled with 2.5 ml of microbeads suspended in a solution of sodium alginate.

Hepatocyte Isolation

Rat liver cells were isolated from 125-150 g male Wistar rats from Charles River Breeding Lab. Inc. (Montreal, Qc.) following the method described by Seglen P. O. (*Methods Cell Biol.*, 1976, 13:29-83). Each rat was anaesthetized with sodium pentobarbital and cannulated via the portal vein. Subsequently, the thoracic vena cava was cut and the liver was perfused with the calcium free perfusion buffer (142 mM NaCl, 6.7 mM KCl, 10 mM HEPES, 20 mM fructose, pH 7.4) for 10 min. at 40 ml/min. Afterwards, the liver was perfused with the collagenase perfusion buffer (67 mM NaCl, 6.7 mM KCl, 100 mM HEPES, 20 mM fructose, 5 mM $CaCl_2$, 0.05% collagenase, pH 7.5) for an additional 15 min. at 25 ml/min. The liver was then excised, placed in William's E medium supplemented with 100 ug/ml streptomycin and penicillin, and gently shaken to free loose liver cells from the liver tissue. The cells were collected, filtered through a 74 um nylon monofilament mesh (Cistron Corp.; Elmford, N.Y.), and centrifuged at 50 G for 5 min. to remove connective tissue debris, cell clumps, non-parenchymal cells, and damaged cells. The cell pellet was then resuspended in Percoll® and centrifuged at 50 G for 10 min. as described by Smedsrod S. et al. (*J. Leuk. Biol.*, 1985, 38:213-30). The hepatocyte cell fraction was collected and washed several times with media to remove traces of extraneous extracellular material.

Encapsulation

The isolated hepatocytes were prepared for encapsulation by washing the cells with saline, and then resuspending the cells in 4.0% sodium alginate (4.0% sodium alginate, 0.9% saline, 20 mM fructose). The final concentration of cells and sodium alginate were adjusted accordingly with saline to obtain the working concentrations of $20 \times 10^6$ cells/ml and 2.0% respectively.

The macroencapsulation of hepatocytes was then carried out in two steps. First, the hepatocytes suspended in sodium alginate were entrapped within a solid calcium alginate microbead. This was done by filling a 5.0 ml syringe (Becton Dickinson & Co.; Rutherford, N.J.) with the cell suspension and extruding the sample with a syringe infusion pump (Harvard Apparatus; Millis, Mass.) through the first droplet generator. The droplets formed at the end of the sample jet were allowed to fall dropwise into a beaker containing 200 ml 100 mM $CaCl_2$ (100 mM $CaCl_2$, 10 mM HEPES, 20 mM fructose, pH 7.4). A strainer cup was fitted inside the beaker to collect the droplets and to facilitate the removal of the formed microbeads. The microbeads were allowed to harden for approximately 15 min. After which they were removed and temporally stored in Hank's Balanced Salt Solution (Gibco Laboratories; Burlington, Ont.) supplemented with 10% 100 mM $CaCl_2$ solution. Periodically every 15 min., the cells in the syringe were checked and resuspended to minimize the effect of cell sedimentation. The air flow and infusion rate through the droplet generator were 2.0-3.0 l/min. and 0.013-0.026 ml/min. respectively; and the clearance height between the end of the sample jet the surface of the calcium solution was set approximately 4 cm.

The microbeads were then macroencapsulated as follows. We first washed 1.0 ml (settled volume) of microbeads with buffered saline (0.9% NaCl, 10 mM HEPES, pH 7.4). The saline was aspirated and 1.0 ml 1.5% sodium alginate was added to the 1.0 ml of microbeads. The 1.5% alginate was prepared by diluting the 4.0% stock solution of sodium alginate with buffered saline. With a 5.0 ml syringe, the length of the PTFE capillary tubing was filled with the alginate and suspension of microbeads. The tapered end of the capillary tubing was inserted through the top of the sample jet of the second droplet generator until the tip of the tubing extended approximately 15 mm beyond the end of the sample jet. With the syringe still attached to the other end of the tubing, the suspensions of microbeads in the tubing was extruded with the Harvard infusion pump. Similarly, the drops formed at the end of the sample jet were allowed to fall dropwise into a beaker containing a strainer cup and filled with 200 ml of 100 mM $CaCl_2$. The macrobeads were allowed to cure in the calcium solution for approximately 15 min. After which, they were removed and washed with buffered saline.

The air flow and extrusion rates through the modified droplet generator were 7.0–9.0 l/min. and 0.072–0.140 ml/min. respectively. The tip to the capillary tubing was set approximately 5.0 cm above the surface of the calcium solution.

The alginate matrix on the surface of the macrobead was stabilized with poly-l-lysine by immersing the macrobead in 80 ml 50 mg % solution of poly-l-lysine (50 mg % poly-l-lysine, 0.9% NaCl, 10 mM HEPES, 20 mM fructose, pH 7.4) for 15 min. The macrobeads were then drained, washed with buffered saline, and immersed into 200 ml 0.1% sodium alginate (0.1% sodium alginate, 0.9% NaCl, 10 mM HEPES, 20 mM fructose, pH 7.4) for 15 min. to apply an external layer of alginate. After 15 min., the macrobeads were collected and immersed in 200 ml 50 mM sodium citrate (50 mM sodium citrate, 0.8% NaCl, 20 mM fructose, pH 7.4) to solubilize the intracapsular calcium alginate. This required up to 30 min. with frequent changing of the citrate solution. The resulting macrocapsules were then washed with saline before intra-peritoneal implantation into mice. Microcapsules were made by following the above procedures and appropriately suing microbeads in the place of the macrobeads.

Implantation

Prior to implantation, the microcapsules or macrocapsules were first washed with non-pyrogenic saline. The ends of 1.0 ml syringes (Becton Dickinson & Co.; Rutherford, N.J.) were plugged and filled thorugh the top with 0.6–0.8 ml (settled volume) of either microcapsules or macrocapsules. In anaesthetized CD-1 mice (Charles River Breeding Lab. Inc.; Montreal, Qc.), part of the abdomen was shaved and the capsules were injected into the peritoneal cavity through a small hole cut into the abdominal wall to fit the end of the syringe. The edge of the hole was immediately sutured and clipped to close the wound. After a set number of days, mice were sacrificed and the number of free floating unaggregated capsules were retrieved by peritoneal lavage. The capsules were washed with saline to remove loose peritoneal cells suspended in the peritoneal washings. The capsules were then transferred into a 1.0 ml syringe and the settled volume of the recovered capsules were measured.

EXAMPLE II

Proceeding in the same manner as in Example I, but substituting hepatocytes by at least one selected from the group consisting of pancreatic cells, thyroid cells, liver cells, erythrocytes, leucocytes, platelets, albumin, antigens, antibodies, collagen, plasma, red blood cells, and other materials; there is obtained microcapsule containing one or more of the above materials.

It should be understood, however, that this detailed description, while indicating preferred embodiments of the invention, is given by way of illustration only since various changes and modifications within the spirit and scope of the invention will become apparent to those skilled in the art.

We claim:

1. In a method for encapsulating biologically active material within a semipermeable capsule wherein gelled beads are obtained by suspending said material in a solution of water-soluble substance which can be reversibly gelled, forming said solution into droplets, and gelling said droplets to produce discrete shape-retaining temporary gelled beads; the improvement comprising the steps of:

a) suspending said gelled beads in a solution of a water-soluble substance which can be reversibly gelled;
   b) forming droplets which contain one or more of the gelled beads of step a);
   c) gelling said droplets of step b) to produce discrete shape-retaining temporary gelled beads which contain said gelled beads of step a);
   d) forming semi-permeable membranes on each gelled bead of step c), thereby preventing the incorporation of any biologically active material from said gelled beads of step a) into said membranes; and
   e) reliquifying the gel within said membranes, thereby dispersing the content of said gelled beads of step a) within said capsule.

2. The method according to claim 1, wherein said water-soluble substance which can be reversibly gelled is a gum.

3. The method according to claim 2, wherein said gum has free acid functional groups and said membrane formation step is effected by contacting the temporary capsules with a polymer of a molecular weight between 3,000 and 100,000 daltons and having free amino functional groups with cationic charge, said contacting being effective to form permanent crosslinks between said free amino groups of said polymer and acid functional groups in a surface layer of the capsule.

4. The method according to claim 3, wherein said polymer is selected from the group consisting of: polylysine, polyethylenimine, polyarginine, and polymer containing quaternary ammonium groups, said polymer having an average molecular weight of about 15,000 to 35,000 daltons.

5. The method according to claim 2, wherein said gum is selected from the group consisting of: alkali metal alginate, carrageenan and gelatin.

6. The method according to claim 5, wherein said alkali metal alginate is sodium alginate and said gelling of the droplets is effected by using a calcium solution.

7. The method according to claim 6, wherein reliquifying the gel is effected by removing the calcium ions contained within said gelled beads, thereby resolubilizing the gelled alginate interior of the membranes of said capsule including said gelled beads contained therein.

8. The method according to claim 1, wherein said gelling of the droplets is effected by using calcium ions, alkaline ions, lowering the temperature to below the gelling temperature, or by changing the pH.

9. The method according to claim 1, wherein said reliquifying of the gel is effected by using a chelating agent, increasing the temperature to above the gelling temperature, or by changing the pH.

10. The method according to claim 1, wherein said biologically active material is selected from the group consisting of: viable cells, viable tissues, proteins, immunoproteins, peptides, hormones and drugs.

11. The method according to claim 10, wherein said viable cells are selected from the group consisting of: liver cells, endocrine cells, pancreatic cells, erythrocytes, leucocytes and platelets.

12. The method according to claim 11, wherein said liver cells include hepatocytes and Kupffer cells, said endocrine cells include thyroid tissue cells and said pancreatic cells include islet cells.

13. The method according to claim 10, wherein said viable tissues selected from the group consisting of: endocrine tissues and liver tissues.

14. The method according to claim 1, wherein said gelled beads of step a) vary in diameter between $1\mu$ and 1 mm and said gelled beads of step c) vary in diameter between $2\mu$ and 10 mm.

15. A semipermeable capsule obtained according to the method of claim 1 wherein its membrane is devoid of any encapsulated material embedded or protruding therein.

16. A semipermeable capsule obtained according to the method of claim 1 suitable for implantation in a mammalian host and containing one or more viable, healthy physiologically active living tissue cells or other biologically active material, said capsule on implantation being impermeable to said host immune system proteins or immune system cells but permeable to tissue nutrients and to metabolites or secretions produced by said encapsulated tissue or biologically active material, thereby said capsules being devoid of aggregation and of immunological reactions of said host.

* * * * *